United States Patent

Kodama

[11] Patent Number: 5,938,445
[45] Date of Patent: Aug. 17, 1999

[54] KIT FOR MANUFACTURING OCCLUSAL PLANE RAISING PLATE

[76] Inventor: Goji Kodama, 20-12, Kitakasai 1-chome, Edogawa-ku, Tokyo, Japan

[21] Appl. No.: 08/943,150

[22] Filed: Oct. 3, 1997

[30] Foreign Application Priority Data

Oct. 3, 1996 [JP] Japan ..................................... 8-281246

[51] Int. Cl.⁶ ................. A61C 5/00; A61C 5/14
[52] U.S. Cl. .............................. 433/215; 433/37; 128/861
[58] Field of Search ................................ 433/37, 71, 215; 128/861, 862, 859

[56] References Cited

U.S. PATENT DOCUMENTS

| | | | |
|---|---|---|---|
| 1,840,703 | 1/1932 | Cunningham | 433/71 |
| 3,488,848 | 1/1970 | Lerman | 433/215 |
| 3,532,091 | 10/1970 | Lerman | 128/861 |
| 4,531,914 | 7/1985 | Spinello | 433/80 |
| 4,551,135 | 11/1985 | Gorman et al. | 433/80 |
| 4,763,791 | 8/1988 | Halverson et al. | 433/37 |
| 5,103,838 | 4/1992 | Yousif | 128/859 |
| 5,137,448 | 8/1992 | Dougherty et al. | 433/37 |
| 5,511,562 | 4/1996 | Hancock | 128/861 |

FOREIGN PATENT DOCUMENTS

| | | |
|---|---|---|
| 0298649 | 1/1989 | European Pat. Off. . |
| 62-38985 | 8/1987 | Japan . |
| 9317631 | 9/1993 | WIPO . |
| 9514449 | 6/1995 | WIPO . |

Primary Examiner—John J. Wilson
Attorney, Agent, or Firm—Browdy and Neimark

[57] ABSTRACT

The invention has an object to permit easy and rapid manufacture of an occlusal plane raising plate which does not contain a fluid therein and does not impair relative movement of the upper and lower jaws, and provides a kit for manufacturing an occlusal plane raising plate comprising an occlusal plane raising plate manufacturing member body composed of a soft and thin lower member, an upper member inferior in softness to the lower member, and a path capable of housing a hardenable material, and hardenable materials to achieve the above object.

11 Claims, 5 Drawing Sheets

KIT FOR MANUFACTURING OCCLUSAL PLANE RAISING PLATE

BACKGROUND OF THE INVENTION

1. Field of the Invention

The present invention relates to a kit for manufacturing an occlusal plane raising plate (splint) used by inserting between maxillary and mandible dental arches, easily and in a short period of time, and an occlusal plane raising plate manufactured by means of such a kit.

2. Description of the Related Art

The general attention is now attracted by symptoms known as arthrosis to temporomandibular joint. These symptoms are attributable to a long tension of muscles including temporal muscle, masseter muscle, lateral pterygoid muscles, medial pterygoid muscle, sternocleid mastoid muscle and trapezius muscles around the temporomandibular joint caused by clenching or gnashing of teeth unconsciously conducted under persisting stress or hard tensioning of the muscles of facial expression.

Clenching or gnashing of teeth unconsciously conducted under stress are called "bruxism" which may occur not only during sleep but also during wakening, and the number of automobile drivers and particularly computer operators who unconsciously clenches their teeth has recently increased. Upon occurrence of bruxism, the maxilla and mandible teeth bite with a maximum occlusal force, so that, in a person having malocclusion or a trouble in occlusion, suffers from more frequent occurrence of arthrosis of temporomandibular joint, and the condition of disease is believed to worsen.

Direct symptoms of arthrosis of temporomandibular joint include various muscular pains, muscular fatigue and muscular spasm around the temporomandibular portion as described above, and indirect symptoms include autonomic dysfunction, irritation or feeling of discomfort of which the cause is unknown, languor, stiffness of the shoulders, lumbago, chronic headache, numbness of the limbs, hypertension, some symptoms of diabetes mellitus, gastric ulcer, duodenal ulcer, arrhythmia, angina pectoris, articular rheumatism, lack of patience or concentration, and various other symptoms are believed to be attributable to abnormal tonus of muscles or malocclusion.

Several means for alleviating these symptoms of arthrosis of temporomandibular joint have conventionally proposed, but none are satisfactory.

For example, Japanese Patent Publication No. S62-38, 985(38,985/1987) discloses an orthodontic appliance which is arranged intraorally, and alleviates compression and pain caused by muscles of mastication resulting from the difference in biting pressure along the upper and lower dental arches. This orthodontic appliance comprises an elastic body provided with a fluid housing path therein and the fluid housed therein hydrostatically compensates a pressure difference produced from the occlusal force. However, since this orthodontic appliance has a configuration in which a fluid such as water is sealed in the elastic body, the appliance may be broken during use and the fluid housed therein may flow out into the oral cavity. Particularly when the upper and lower dentitions bite with the maximum biting force as in the case of bruxism described above, the appliance cannot withstand it.

The U.S. Pat. No. 3,488,848 and No. 3,532,091 also disclose orthodontic appliances similar to that of JP S62-38,985. These orthodontic appliances have a configuration comprising an elastic body housing a fluid therein, and have a problem in that there is a risk of the fluid therein flowing out upon breakage thereof during use, and further, there is taken no counter- measure against bruxism.

Further, there is available an occlusion plane raising plate prepared by hardening a hardenable material in agreement with the shape of teeth of the patient, i. e., a dentist copies the shape of upper and lower dentitions of the patient, and separately manufactures a raising plate on the basis thereof. This occlusion plane raising plate is defective in that it requires a long time and technical skill for manufacture.

The present invention was developed to solve the defects of the conventional art as described above, and has an object to permit easy manufacture in a short period of time an occlusal plane raising plate which eliminates the risk of an internal fluid flowing out during use, and is effective also for bruxism.

SUMMARY OF THE INVENTION

The present invention solves the foregoing problems by providing a kit for manufacturing an occlusal plane raising plate having at least an occlusal plane raising plate manufacturing member body comprising at least a soft and thin lower member and an upper member inferior in softness to the lower member, and having a hollow portion capable of housing a hardenable material therein.

The kit for manufacturing an occlusal plane raising plate of the invention may further be provided with a hardenable material. The hardenable material is injected or arranged in the hollow portion of the occlusal plane raising plate manufacturing member body, and hardened under a hydrostatic pressure caused by biting, thus permitting manufacture of an occlusal plane raising plate having a shape meeting that of the patient teeth. Because injection is accomplished by relatively simple means and the hardenable material hardens quickly, anyone can easily manufacture an occlusal plane raising plate. The occlusal plane raising plate of the invention comprises a hardenable material, thus eliminating the risk of the internal fluid flowing out upon breakage during use.

The lower member of the occlusal plane raising plate manufacturing member body of the invention is manufactured with a soft and thin material. The lower member can therefore be deformed in agreement with the biting surface of the mandible dentition in contact of the patient, so that the shape of the biting surface of the mandible dentition is accurately copied onto the hardening surface of the hardenable material.

On the other hand, the upper member of the occlusal plane raising plate manufacturing member body of the invention is made of a material inferior in softness to the lower member. Deformation of the upper member is therefore to such an extent that only an indentation the laryngeal top of the maxillary dentition in contact are impressed. As a result, the hardened surface corresponding to the maxillary dentition of the patient, having some laryngeal indentations, has substantially a flat surface.

The hardened hardenable material is used as an occlusal plane raising plate after peeling (or without peeling) of the occlusal plane raising plate manufacturing member body having contained the hardenable material.

The occlusal plane raising plate manufactured from the manufacturing kit of the invention, of which the lower surface accurately corresponds to projections and cavities on the biting surface of the mandible dentition of the patient, perfectly fits the mandible dentition and a deviation never occurs. On the other hand, the upper surface of the occlusal plane raising plate manufactured by means of the manufacturing kit of the invention is substantially flat except for some indentations on the maxillary laryngeal top of the patient, and only roughly copies the shape of the upper biting surface. It is therefore possible for the maxillary dentition to slide in forward/back and right/left directions. This is one of the remarkable features of the invention: this allows the patient to freely move the maxilla and mandible in forward/back and right/left directions during attachment of the occlusal plane raising plate of the invention by providing a degree of freedom to some extent to the upper surface of the occlusal plane raising plate. As a result, the patient is never subjected to an unnecessary stress, and a bruxism such as clenching or gnashing of teeth during sleep or during waking is never transmitted directly to the other teeth or jaws.

The term "soft and thin" as used herein means a property of material which permits deformation in agreement with slight projections and cavities of the biting surface upon light biting by housing the hardenable material in the interior as described above. Being inferior in softness means, upon biting by housing the hardenable material in the interior, a property of the material which does not deform in agreement with fine projections and cavities of the biting surface so much as the soft and thin material, i.e., deforms only to an extent that only indentations of the laryngeal top are impressed at most.

The terms the "upper member" and the "lower member" are relative and do not mean that the upper member is always above the lower member during use. As described later, it is possible to use the lower member in contact with the maxillary dentition and the upper member in contact with the mandible dentition: the occlusal plane raising plate of the invention can be used as the occlusal plane raising plate for the mandible dentition by causing the same to perfectly fit the mandible dentition as described above, or as the occlusal plane raising plate for maxillary dentition by causing the same to be perfectly fit the maxillary dentition.

DESCRIPTION OF THE PREFERRED EMBODIMENTS

Figure 1:
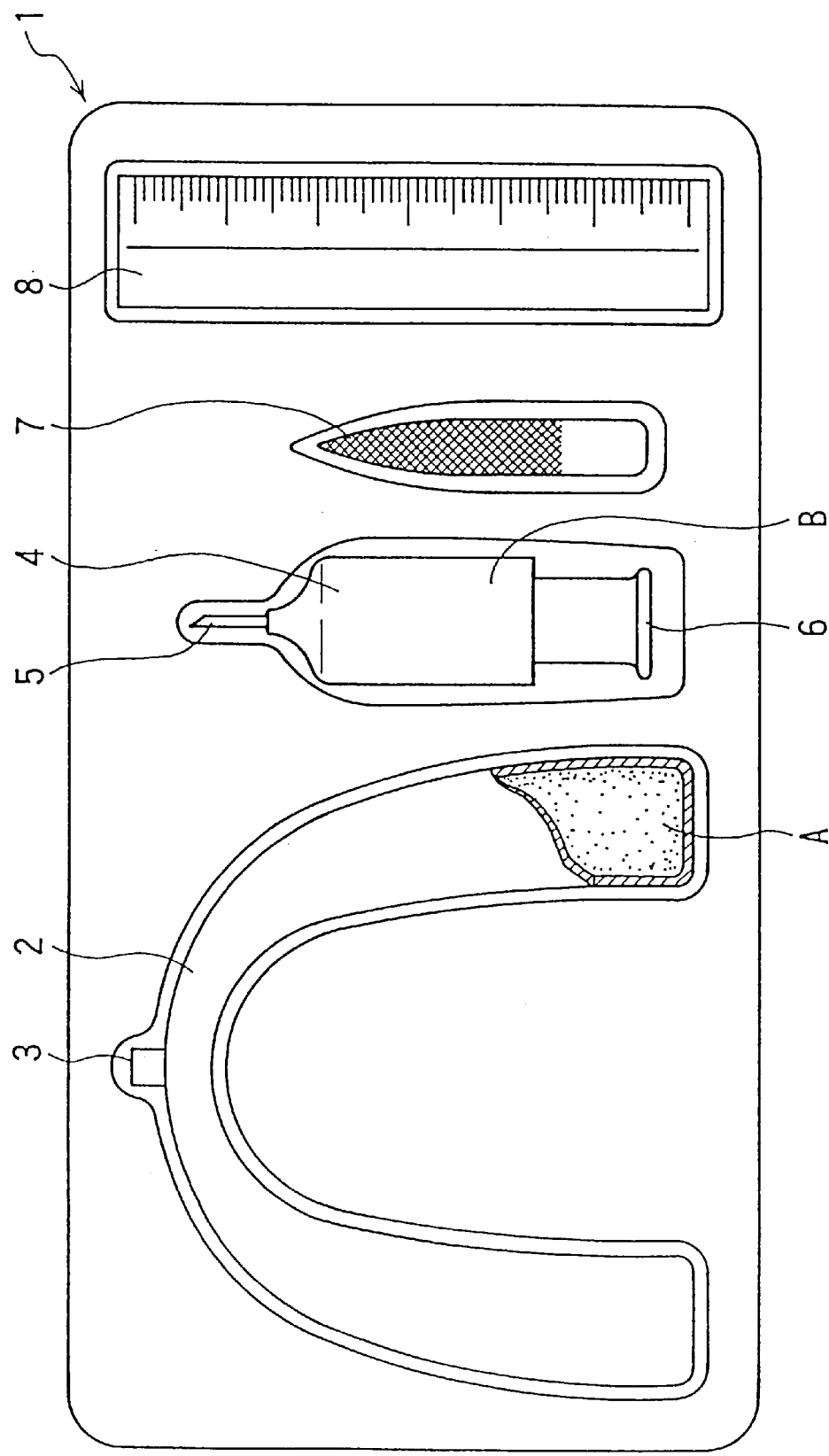
FIG. 1 illustrates an embodiment of the kit for manufacturing an occlusal plane raising plate according to the invention.

The kit for manufacturing an occlusal plane raising plate of the invention may comprise the elements, for example, as shown in FIG. 1. More specifically, in FIG. 1, the kit for manufacturing cm occlusal plane raising plate represented by the reference numeral 1 comprises an occlusal plane raising plate manufacturing member body 2, a hardenable material syringe 4. a file 7, and a rule 8. A material A (powder in this case) of the hardenable materials is previously housed in the occlusal plane raising plate manufacturing member body 2 as shown by a partially cutaway view, and the hardenable material syringe 4 is filled with another material B (liquid in this case) of the hardenable materials. The reference numeral 3 is an injection port of the hardenable material, provided in the occlusal plane raising plate manufacturing member body 2; 5 is a needle for the hardenable material syringe; and 6 is a piston of the hardenable material syringe.

The file 7 is for forming the hardened occlusal plane raising plate by grounding off a trace of the injection port 3, and the rule 8 is for measuring the size of the maxillary and mandible dental arches of the patient. Knowing the size of his or her dental arch, the patient can easily select befitting one from among occlusal plane raising plate manufacturing member bodies 2 of various sizes previously prepared as described later.

In this embodiment, the kit for manufacturing an occlusal plane raising plate 1 comprises the occlusal plane raising plate manufacturing member body 2, the hardenable material syringe 4, the file 7 and the rule 8. As required, the kit may comprise only the occlusal plane raising plate manufacturing member body 2. In this case, a separately prepared hardenable material is injected into the occlusal plane raising plate manufacturing member body 2 by means of a separately prepared hardenable material syringe.

Figure 2:
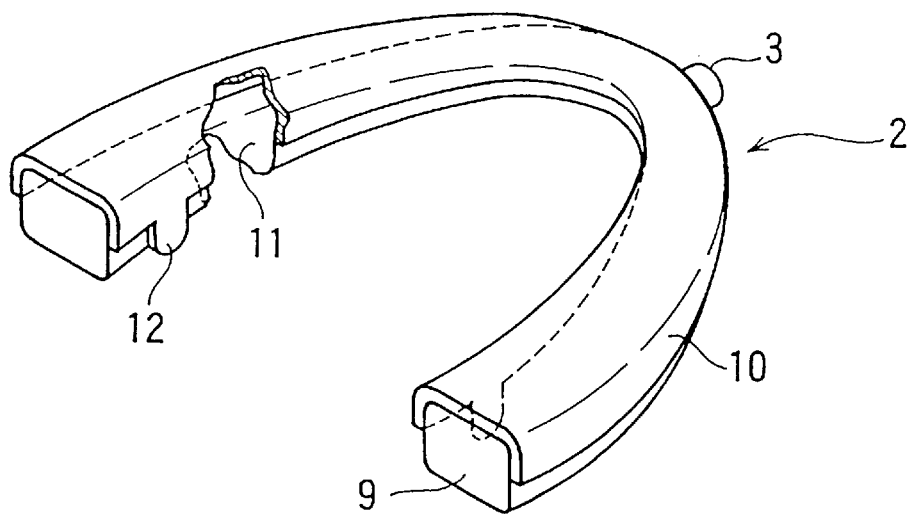
FIG. 2 is a perspective view illustrating an occlusal plane raising plate manufacturing member body.

FIG. 2 illustrates the occlusal plane raising plate manufacturing member body 2 only as derived from the kit. The same reference numerals as in FIG. 1 are assigned to the same members. In FIG. 2, 9 is a lower member of the occlusal plane raising plate manufacturing member body 2, and 10 is an upper member of the occlusal plane raising plate manufacturing member body 2. The lower member 9 and the upper member 10 are liquid- tightly connected to each other by connecting means such as a heat seal or an adhesive, and has a hollow portion 11 for housing the hardenable material therein. The reference numeral 12 is a peeling rip for stripping off the lower member 9 from the upper member 10 after hardening of the hardenable material.

The lower member 9 is relatively soft, made into a small thickness, and when inserted between the upper and lower dentitions and lightly bitten, is deformed, tightly following the shape of the biting surface of the mandible dentition 13 in contact. The material for the lower member should be harmless to human health since it is inserted into the oral cavity. So far as this condition is satisfied, any material may be used: preferable material is a film of synthetic resins such as polyethylene, polypropylene, polyvinylidene chloride, polyvinyl chloride, polybutadiene, nylon, and polyethylene glycol terephthalate. The thickness should be the smallest possible. It should preferably be up to 100 μm, or more preferably, up to 30 μm, or further more preferably, up to 10 μm.

Figure 3:
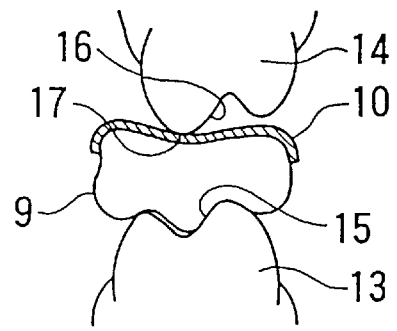
FIG. 3 illustrates a process of deformation of the occlusal plane raising plate manufacturing member body upon light biting.

On the other hand, the upper member 10 is manufactured so as to be thicker than, and inferior in softness to, the lower member 9. Even when it is inserted between the upper and lower dentitions and lightly bitten, as shown in FIG. 3, the upper member 10 does not deform by following the shape of the biting surface 16 of the maxillary dentition 14, and the deformation thereof is such that only an indentation of the laryngeal top (maxillary lingual cusp in FIG. 3) represented by the reference numeral 17. A film of a synthetic resin such as polyethylene, polypropylene, polyvinylidene chloride, polyvinyl chloride, polybutadiene, nylon, or polyethylene glycol terephthalate, which is harmless to human health is used as the material therefor as in the lower member 9. Among others, a slightly thick polyvinyl chloride film or a polyethylene film is particularly suitable. The thickness thereof, depending upon softness of the material, should preferably be such that the film keeps substantially flat when lightly bitten and a hydrostatic pressure is applied from inside. When it is difficult to achieve prescribed properties with a single-layer film, films of the same material or of different materials may be used in lamination.

While FIG. 3 illustrates a case where the lower member 9 is in contact with the biting surface 15 of the mandible dentition 13, and the upper member 10 is in contact with the biting surface 16 of the maxillary dentition 14, a reverse relationship may also be applied. More specifically, the top/bottom relationship of the occlusal plane raising plate manufacturing member body 2 is reversed and the member body 2 is inserted between the upper and lower dentitions of the patient to accurately copy the shape of the biting surface 16 of the maxillary dentition 14. The upper member 10 copies, on the other hand, the shape of the biting surface of the mandible dentition 13 to such extent that an indentation of the laryngeal top is impressed.

Figure 4:
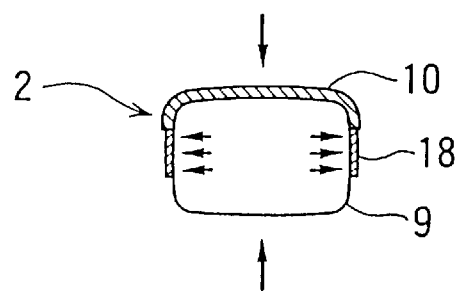
FIG. 4 illustrates another embodiment of the occlusal plane raising plate manufacturing member body.

The occlusal plane raising plate manufacturing member body 2 of the invention may have an intermediate member 18 below the upper member 10 and on a side of the lower member 9, for example, as shown in FIG. 4. The intermediate member 18 is made of a material inferior in softness to that of the lower member. When a biting pressure is applied as shown in by the upward and the downward arrows upon manufacturing an occlusal plane raising plate, the intermediate member 18 has an effect of preventing the sides of the occlusal plane raising plate manufacturing member body 2 from expanding unnecessarily in the transverse direction. The extent of softness of the intermediately member 18 should preferably be between the upper member 10 and the lower member 9, but may be of the same order as that of the upper member 10.

Figure 5:
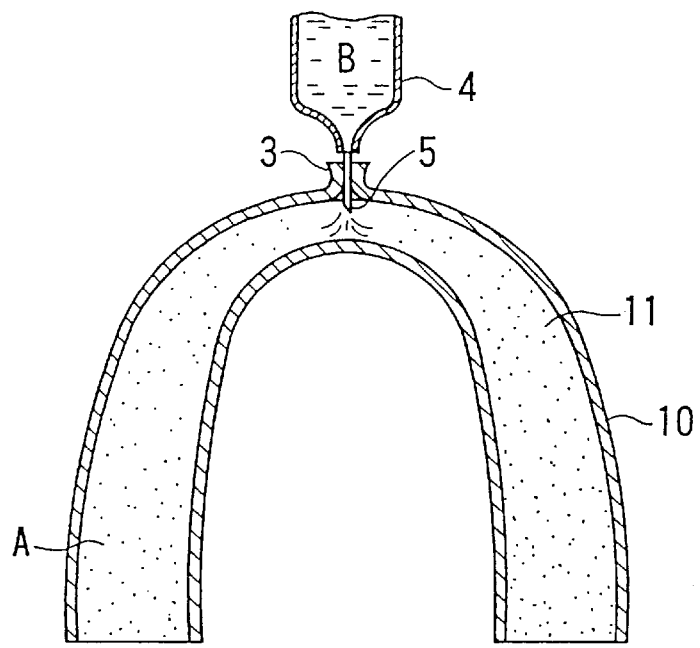
FIG. 5 is a sectional view illustrating another embodiment of the occlusal plane raising plate manufacturing member body and insertion of a syringe.

FIG. 5 is a horizontal sectional view of the occlusal plane raising plate manufacturing member body 2, illustrating insertion of the hardenable material syringe 4 into the injection port 3. The injection port 3 can communicate with the internal hollow portion 11 upon penetration of the needle 5 of the hardenable material syringe 4 as shown in FIG. 5. Upon removal of the needle 5, the injection port 3 restores the original position by the elasticity thereof and clogs up the penetration path of the needle 5. In FIG. 5, the injection port 3 is integrally formed from the material for the upper member 10. When elasticity of the upper member 10 may cause a problem, an injection port 3 may be separately manufactured from an elastic rubber and connected to the upper member 10. Clogging of the injection port 3 after injection of the hardenable material may be accomplished by pressing the injection port 3 with fingers or by twisting.

Although any hardenable material may be used, the material should be harmless to human health since it is used in the oral cavity. The hardenable material should preferably be an instant polymerization resin or a photopolymerization resin used for dental purposes such as methyl methacrylate. An instant polymerization resin is usually present in two forms of powder and liquid, contact or mixing of which causes instant polymerization, leading to hardening. A photopolymerization resin is polymerized and hardened by light.

The above embodiment comprises the steps of previously filling the internal hollow portion 11 of the occlusal plane raising plate manufacturing member body 2 with the powdery material A, and upon use, injecting the liquid material B into the hollow portion 11 by means of the hardenable material syringe 4. The injecting timing and the injecting means are not limited to the above, but vary with the hardenable material used. For example, when two materials starting hardening with mixing or contact are both liquids, the both materials may be injected into the hollow portion 11 upon use. It is also possible to charge one of the two materials into a micro-capsule, and previously house it in the hollows portion 11 together with the other material. Upon use, the micro- capsule is broken by a light biting or pressing with fingers, thus causing mixture of the two materials.

When using a photopolymerization resin, the hardenable materials should preferably be housed previously in the occlusal plane raising plate manufacturing member body 2, and as required, wrap the occlusal plane raising plate manufacturing member body 2 and/or the kit 1 for manufacturing an occlusal plane raising plate with a material not allowing transmission of light. Upon use, light is irradiated onto the occlusal plane raising plate manufacturing member body 2 between the upper and lower dentitions of the patient to cause hardening. In this case, it is needless to mention that the hardenable material syringe 4 or the file 7 is not necessary in the kit 1 for manufacturing an occlusal plane raising plate. The occlusal plane raising plate manufacturing member body 2 is naturally made of a phototransmitting material.

Figure 6:
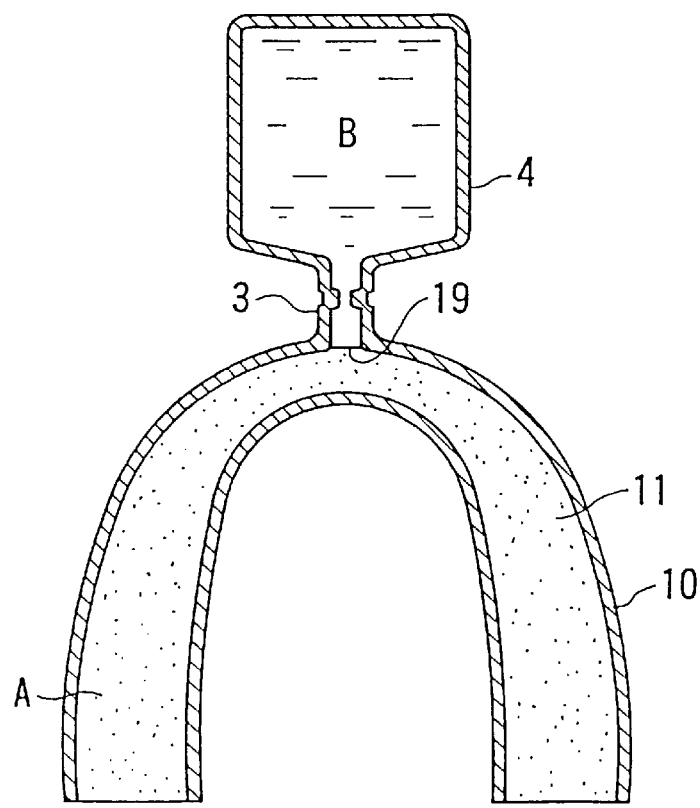
FIG. 6 is a sectional view illustrating further another embodiment of the occlusal plane raising plate manufacturing member body and insertion of a syringe.

FIG. 6 is a sectional view illustrating another embodiment of the hardenable material syringe 4. In this embodiment, the hardenable material syringe 4 and the occlusal plane raising plate manufacturing member body 2 are integrally formed, and the hollow portion 11 is separated from the internal space of the hardenable material syringe 4 by a thin diaphragm 19 so as to permit communication between the two spaces. Presence of this diaphragm 19 prevents contact or mixing of the hardenable material A housed in the hollow portion 11 and the hardenable material B housed in the hardenable material syringe 4. Upon use, pressure in the hardenable material syringe 4 is increased by pressing the hardenable material syringe 4, and finally, the diaphragm 19 permits communication between the two spaces to cause contact and mixing of the hardenable materials A and B to start hardening. After injection, the hardenable material syringe 4 may be wrenched off at the neck portion of the connection with the occlusal plane raising plate manufacturing member body 2, or may be left as it is until the end of hardening.

Upon completion of hardening, the lower member 9 and the upper member 10 of the occlusal plane raising plate manufacturing member body 2 are peeled off from the hardened occlusal plane raising plate by the use of a stripping rip 12 or the like. To smooth peeling, vaseline should previously be coated onto the inside of the lower member 9 and the upper member 10. While it is possible to used the occlusal plane raising plate without peeling of the lower member 9 or the upper member 10, these members are partially broken during use. It is therefore desirable to previously peel off these members 9 and 10.

Figure 7:
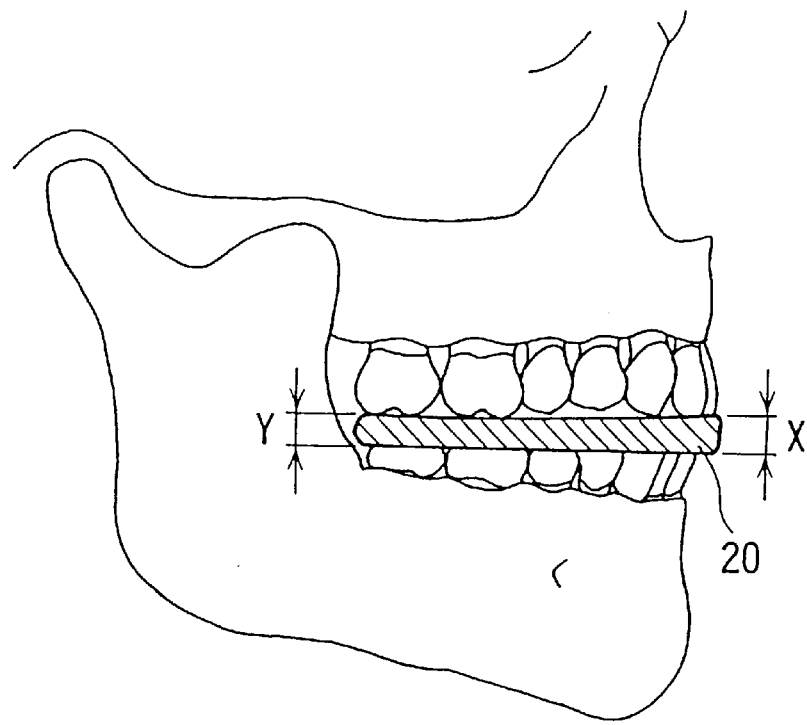
FIG. 7 is a conceptual view illustrating attachment of the occlusal plane raising plate of the invention.

FIG. 7 illustrates the use of the occlusal plane raising plate 20 after peeling of the lower member 9 and the upper member 10. Prior to use, ridges produced after injection of the hardenable materials should preferably be ground off with a file 7 annexed to the manufacturing kit. Attachment may be done during sleep or during wakening, and continuous attachment for a long period of time is preferable.

The occlusal plane raising plate 20 of the invention is used as described above by inserting the same between the upper and lower dentitions, and as a result of attachment of the occlusal plane raising plate 20 of the invention, the upper and lower dentitions of the patient are always kept so that are a distance X at the middle incisor, and a distance Y at the true molar tooth as shown in FIG. 7. The distance X, while depending on a patient, should preferably be within a range of from 3 to 20 mm, and particularly, constant maintenance of a distance within a range of from 6 to 10 mm is preferable because spontaneous discharge during rest is reduced and various symptoms are alleviated. The distance Y should preferably be within a range of from 1.5 to 10mm, and particularly, constant maintenance of a distance within a range of from 3 to 5 mm is preferable because spontaneous discharge during rest is reduced and various symptoms are alleviated. Adjustment of these distances can easily be accomplished by adjusting the volume of the hollow portion 11 of the occlusal plane raising plate manufacturing member body 2 and/or the amount of hardenable materials hardening in the hollow portion 11.

The reason why these distances are particularly preferable is not accurately known. The state in which these preferable distances are maintained is considered to eliminate unnecessary tension in the muscles supporting the maxilla and mandible, and can achieve the most relaxed state. As described above, the occlusal plane raising plate of the invention is effective for keeping the distances between the upper and lower dentitions in the most natural and relaxed state.

In the embodiment shown above, the occlusal plane raising plate has covered the entire biting surface of the upper and lower dentitions. As required, however, the occlusal plane raising plate may cover only the true molar tooth, or only the true molar tooth and the false molar.

Figure 8:
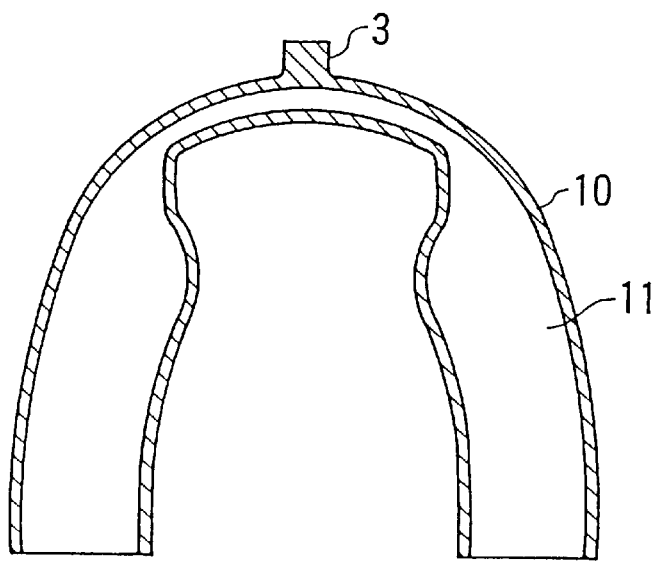
FIG. 8 is a sectional view illustrating another embodiment of the occlusal plane raising plate manufacturing member body.

The embodiment shown in FIG. 8 has a configuration in which the hollow portion 11 of the occlusal plane raising plate manufacturing member body 2 comprises right and left expanded portions and a narrow portion at the center. The narrow portion at the center may as required have a thickness smaller than that of the other portions. The right and left expanded portions have, on the other hand, usual thickness and width, and manufactured so as to cover No. 3 canine and subsequent teeth. Covering at least No. 3 canine with the occlusal plane raising plate of the invention as described above is important from the point of view of practical advantages.

While, in FIG. 8, the right and the left expanded portions communicate to each other, it is also possible to divide the hollow portion 11 into a right and a left portions and provide a hardenable material injection port in each of these portions.

Figure 9:
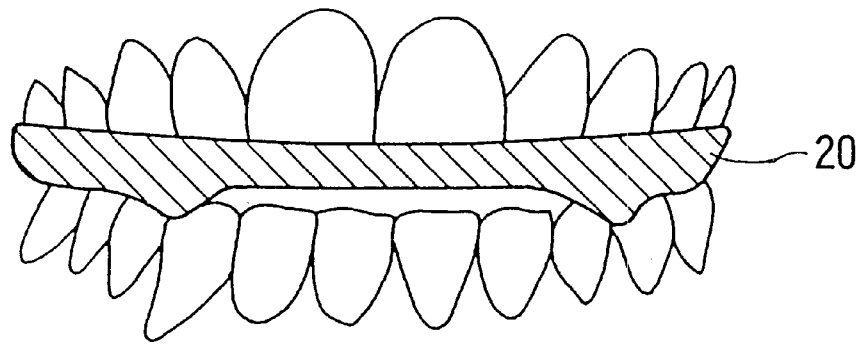
FIG. 9 is a conceptual view illustrating attachment of the occlusal plane raising plate for maxillary dentition.
Figure 10:
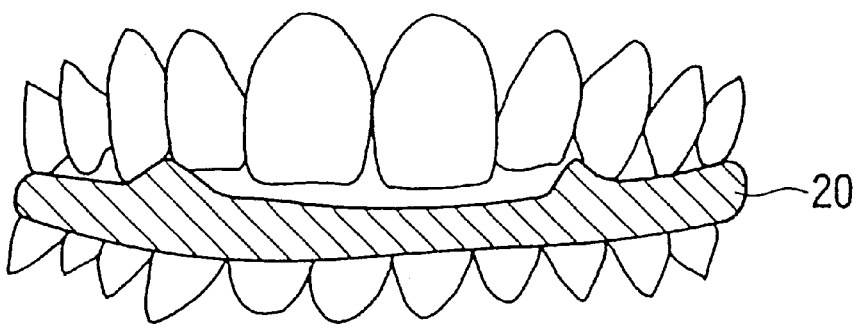
FIG. 10 is a conceptual view illustrating attachment of the occlusal plane raising plate for mandible dentition.

FIGS. 9 and 10 illustrate attachment of an occlusal plane raising plate 20 manufactured by the use of the occlusal plane raising plate manufacturing member body 2 shown in FIG. 8. FIG. 9 illustrates a case of attachment of an occlusal plane raising plate 20 for maxillary dentitions, and FIG. 10, a case of attachment of an occlusal plane raising plate 20 for mandible dentition.

As is clear from FIGS. 9 and 10, upon attaching the occlusal plane raising plate 20 for maxillary dentition, the right and left middle incisors and the right and left side incisors of the mandible dentition do not bite with the maxillary dentition, and a distance is kept between them. Upon attaching the occlusal plane raising plate 20 for mandible dentition, the right and left middle incisors and the right and left side incisors of the maxillary dentition do not cite with the mandible dentition, and a distance is kept between them. Symptoms of arthrosis of temporomandibular joint are further alleviated by preventing the right and left middle incisors and the side incisors of the maxillary or mandible dentition from biting with the corresponding dentition.

The occlusal plane raising plate manufacturing member body 2 has substantially a U-shaped a sectional shape, and should have a shape and size meeting the shape and size of the dental arch of the patient. It is preferable to previously prepare several or several tens of shape patterns on the basis of race, sex and age data, and prepare occlusal plane raising plate manufacturing kits capable of meeting various ages, sexes and races. It is of course necessary to change the amount of hardenable materials in match with the shape and size of the occlusal plane raising plate manufacturing member body 2. By providing several or several tens of occlusal plane raising plate manufacturing kits as described above, it is possible to easily manufacture an occlusal plane raising plate befitting to a patient in a short period of time.

EXAMPLES

Now, the present invention will be described below by means of some examples. It is needless to mention that the present invention is not limited to these examples.

Example 1

An occlusal plane raising plate was manufactured by the use of an occlusal plane raising plate manufacturing kit as shown in FIG. 1.

A polyethylene lap film was used as the lower member, and a polyethylene film having a thickness of about 0.04 mm was used as the upper member. After forming these films into appropriate shapes, the films were bonded to manufacture an occlusal plane raising plate manufacturing member body. An instant polymerization resin "ORTHOFAST" (made by GC Dental Products Co.) was used as the hardenable material, and a powdery material which is the hardening by-product thereof was housed in the hollow portion of the occlusal plane raising plate manufacturing member body upon bonding the lower member and the upper member. On the other hand, an liquid material which is the hardening main product was housed in an injector-like hardenable material syringe, thus completing an occlusal plane raising plate manufacturing kit.

Upon use, the syringe was inserted into an injection port of the occlusal plane raising plate manufacturing member body, and after injecting the hardening main product into the occlusal plane raising plate manufacturing member body, crumbled the resultant product with fingers to promote mixing the of hardenable materials, and in a state in which the materials began hardening into a rice-cake-like condition, the product was inserted between the upper and lower dentitions of a patient. Hardening was started in about 30 seconds, and was completed in a short period of time. Injection and hardening of the hardenable materials took about three minutes. After hardening, it was taken out, and the upper member and the lower member were peeled off. Traces of injection were ground off with a file.

The thus manufactured occlusal plane raising plate was actually attached to a patient: a distance of about 7 mm was kept between the middle incisors, and a distance of about 3 mm, between the true molar teeth. Relative movement in forward/backward and right/eft directions of the upper and lower jaws was relatively free.

Example 2

An occlusal plane raising plate manufacturing member body was manufactured by the use of the same materials as in the Example 1. As the hardenable material, a photopolymerization resin (product name: "CYLAXPLUS#5703J", made by Three-M Chemicals Co.) was used. Prior to completely bonding the upper member and the lower member, the photopolymerization resin was injected from an opening remaining between the upper member and the lower member, and the opening was bonded. The occlusal plane raising plate manufacturing member body was thus manufactured, and covered with a light- shielding sheet to form a kit for manufacturing an occlusal plane raising plate.

Upon use, the occlusal plane raising plate was taken out by tearing the light- shielding sheet, and light was irradiated in a state in which the occlusal plane raising plate was inserted between the upper and lower dentitions of a patient for hardening. A light irradiator commercially known as "OPTILUX 400" (made by Three-M Chemicals Co. and emitting a light having a wave length of 740 nm ) was employed. As the resin hardened in about three minutes after light irradiation, it was taken out and the upper member and the lower member were peeled off. The surface of smooth, free from traces of injection, and grinding with a file was not necessary.

The thus manufactured occlusal plane raising plate was actually attached to the patient. The distance between the middle incisors was kept at about 7 mm and the distance between the true molar teeth was kept at about 3 mm. Relative movement in forward/backward and right/left directions of the upper and lower jaws was relatively free.

According to the kit for manufacturing an occlusal plane raising plate of the invention, as described above, it is possible to manufacture an occlusal plane raising plate very easily and in a short period of time. The resultant occlusal plane raising plate does not contain a fluid such as water so that there is no risk of an internal fluid flowing out in breakage caused by strong biting. In addition, relative movement of upper and lower jaws is possible. It is therefore possible to effectively alleviate or eliminate various symptoms of arthrosis of temporomandibular joint caused by bruxism or malocclusion without giving an unnecessary stress to the patient.

What is claimed is:

1. A kit for manufacturing an occlusal plane raising plate, having at least an occlusal plane raising plate manufacturing member body which comprises at least a soft and thin lower member and an upper member inferior in softness to the lower member, and said lower member and said upper member being connected to each other to form a hollow portion which is substantially liquid tight and capable of housing a hardenable material therein.

2. The kit for manufacturing an occlusal plane raising plate according to claim 1, wherein the occlusal plane raising plate manufacturing member body has an intermediate member inferior in softness to the lower member below the upper member and on a side of the lower member.

3. The kit for manufacturing an occlusal plane raising plate according to claim 1, wherein said kit contains hardenable material.

4. The kit for manufacturing an occlusal plane raising plate according to claim 3, wherein the hardenable material comprises two kinds of material which start hardening through contact or mixing.

5. The kit for manufacturing an occlusal plane raising plate according to claim 4, wherein one of the two materials is previously housed in the hollow portion in the occlusal plane raising plate manufacturing member body.

6. The kit for manufacturing an occlusal plane raising plate according to claim 4, wherein both the two kinds of material are previously housed in the hollow portion in the occlusal plane raising plate manufacturing member body in such state that these materials are not in mutual contact.

7. The kit for manufacturing an occlusal plane raising plate according to claim 3, wherein said kit is provided with means for injecting the hardenable material into the hollow portion in the occlusal plane raising plate manufacturing member body.

8. The kit for manufacturing an occlusal plane raising plate according to claim 7, wherein said means for injection is a hardenable material injecting member having a compressible volume separated from the hollow portion in the occlusal plane raising plate manufacturing member body by a diaphragm capable of achieving communication under pressure.

9. The kit for manufacturing an occlusal plane raising plate according to claim 3, wherein said hardenable material is a photopolymerization resin.

10. The kit for manufacturing an occlusal plane raising plate according to claim 1, wherein said occlusal plane raising plate manufacturing member body has substantially a U-shaped cross-section meeting the shape of a human dental arch.

11. The kit for manufacturing an occlusal plane raising plate according to claim 10, wherein the substantially U-shaped cross-section of the occlusal plane raising plate manufacturing member body is selected from a plurality of patterns previously prepared on the basis of data such as race, sex and age.

* * * * *